(12) United States Patent
Spear et al.

(10) Patent No.: US 7,818,040 B2
(45) Date of Patent: Oct. 19, 2010

(54) DEFLECTABLE MEDICAL THERAPY DELIVERY DEVICE HAVING COMMON LUMEN PROFILE

(75) Inventors: Stanten C. Spear, Arden Hills, MN (US); James F. Kelley, Coon Rapids, MN (US); Johnson E. Goode, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1198 days.

(21) Appl. No.: 10/655,980

(22) Filed: Sep. 5, 2003

(65) Prior Publication Data

US 2005/0054919 A1 Mar. 10, 2005

(51) Int. Cl.
*A61B 8/14* (2006.01)
(52) U.S. Cl. .................. 600/407; 600/467; 600/410; 600/437; 600/438; 600/468; 382/128
(58) Field of Classification Search .............. 600/410, 600/407, 424, 427, 431, 110, 437, 438, 467, 600/468; 607/28–30; 604/164.13; 382/128
See application file for complete search history.

(56) References Cited

U.S. PATENT DOCUMENTS

| | | | | |
|---|---|---|---|---|
| 5,395,328 A | | 3/1995 | Ockuly et al. | |
| 6,004,269 A | * | 12/1999 | Crowley et al. | 600/439 |
| 6,263,244 B1 | | 7/2001 | Mann et al. | |
| 6,297,220 B1 | * | 10/2001 | Leiden et al. | 514/44 |
| 6,638,268 B2 | * | 10/2003 | Niazi | 604/528 |
| 6,704,590 B2 | * | 3/2004 | Haldeman | 600/407 |
| 6,733,500 B2 | * | 5/2004 | Kelley et al. | 606/41 |
| 6,836,687 B2 | * | 12/2004 | Kelley et al. | 607/122 |
| 7,048,711 B2 | * | 5/2006 | Rosenman et al. | 604/95.04 |
| 7,267,650 B2 | * | 9/2007 | Chow et al. | 600/467 |
| 2001/0052345 A1 | * | 12/2001 | Niazi | 128/898 |

\* cited by examiner

*Primary Examiner*—Brian Casler
*Assistant Examiner*—Joel M Lamprecht
(74) *Attorney, Agent, or Firm*—Carol F. Barry

(57) ABSTRACT

A method of locating a target site for delivering a therapy to a patient that includes advancing a delivery device having a steerable portion and a deflectable tip having a tapered portion to an area along a first site. A contrast media is delivered through a thru lumen and outward from a distal end of the delivery device in fluid communication with the thru lumen to position the contrast media along the first site and the delivery device is further advanced toward the first site and within the first site, or the delivery device is further advanced toward the first site and within the first site without the contrast. The contrast media is then delivered from the distal end of the delivery device within the first site to locate the target site.

36 Claims, 15 Drawing Sheets

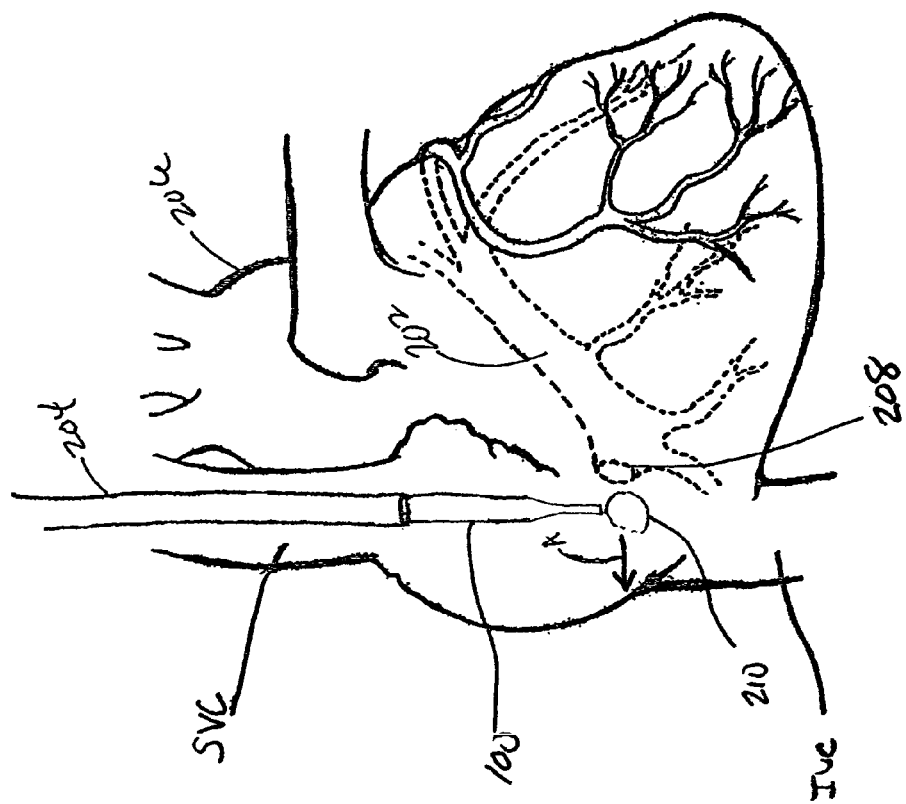

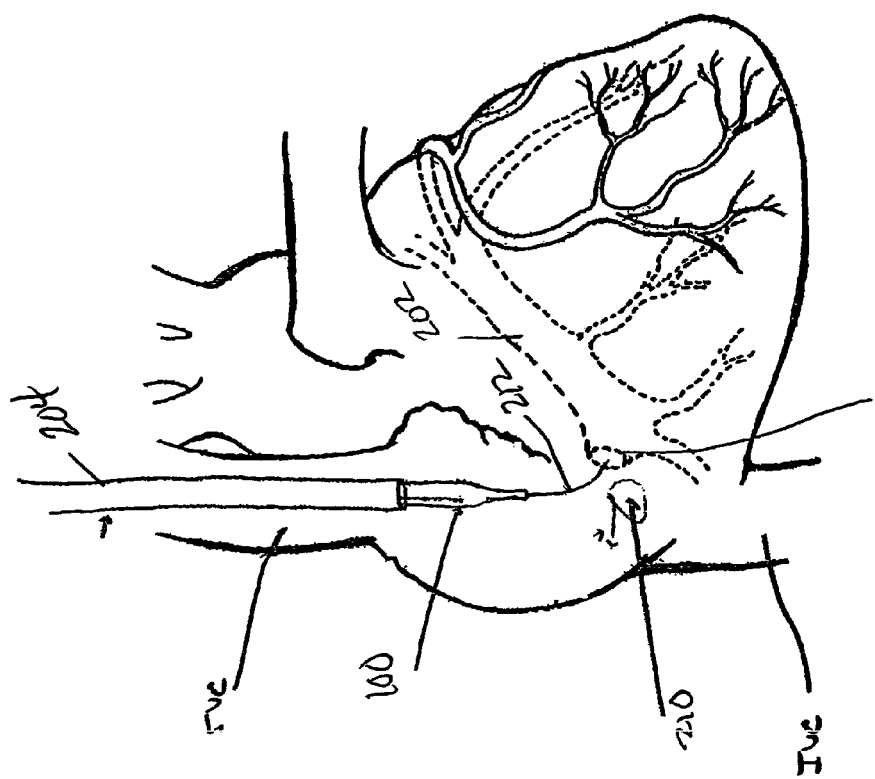

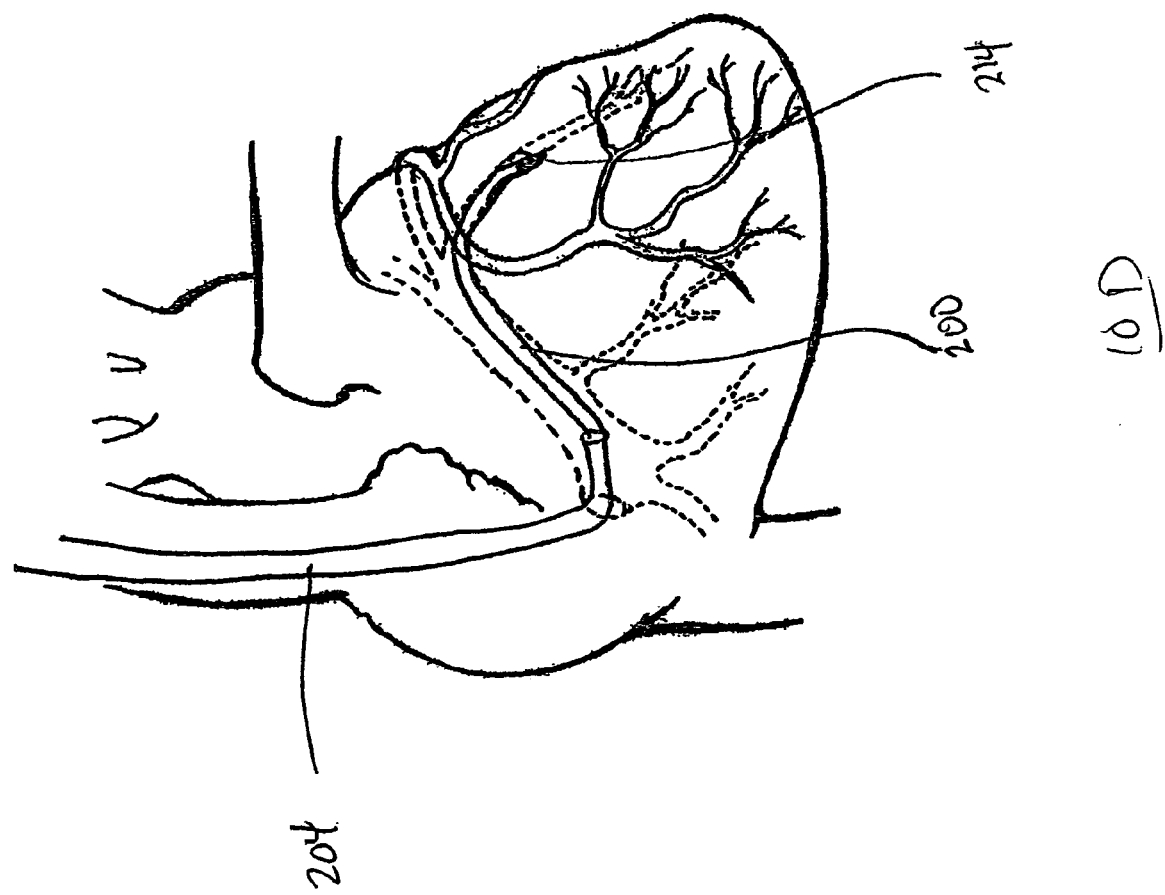

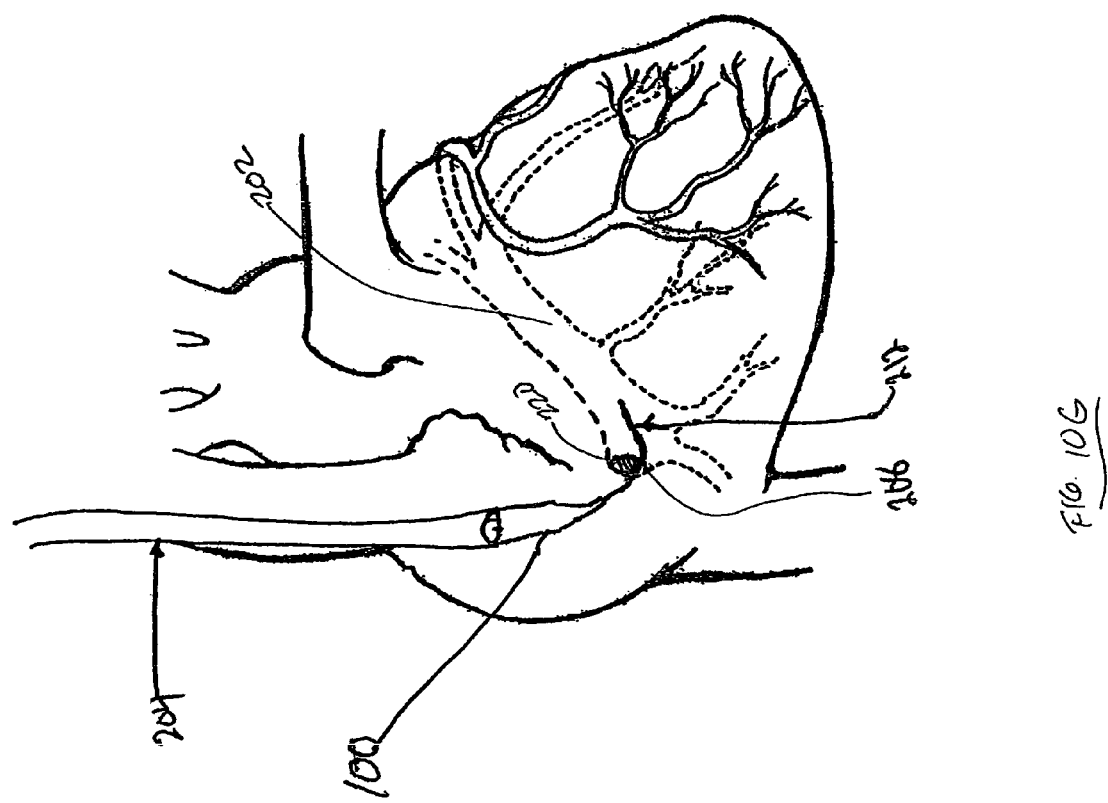

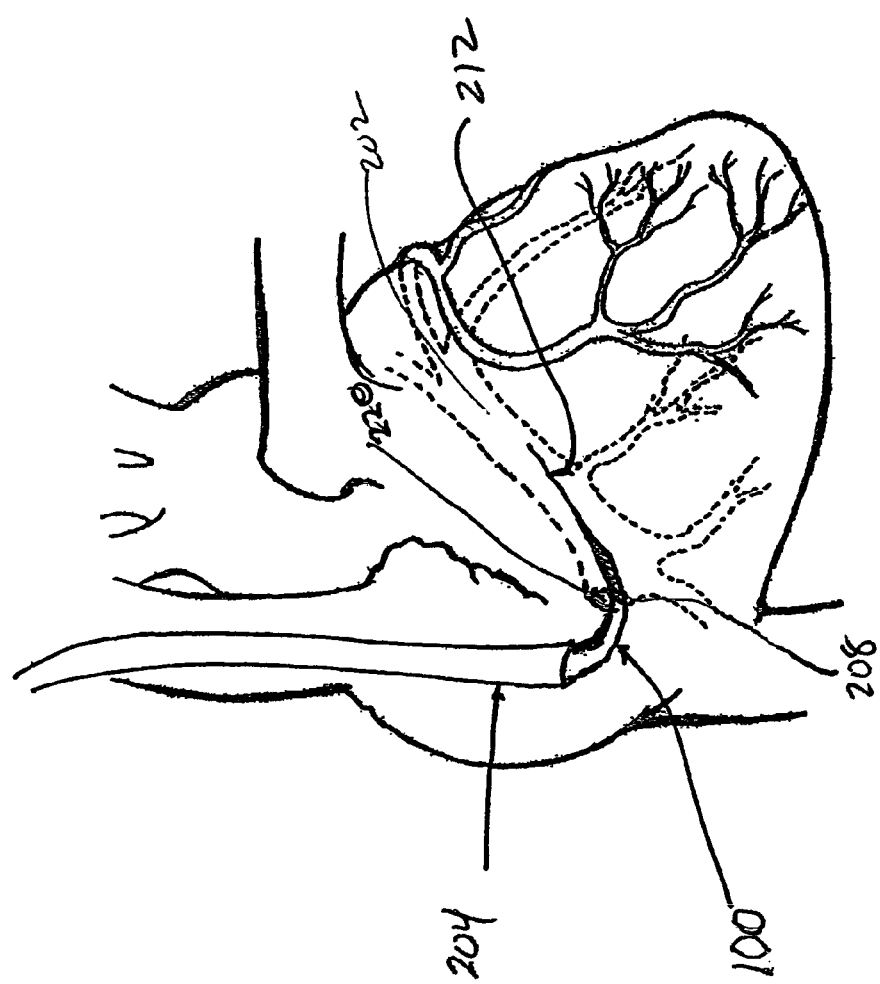

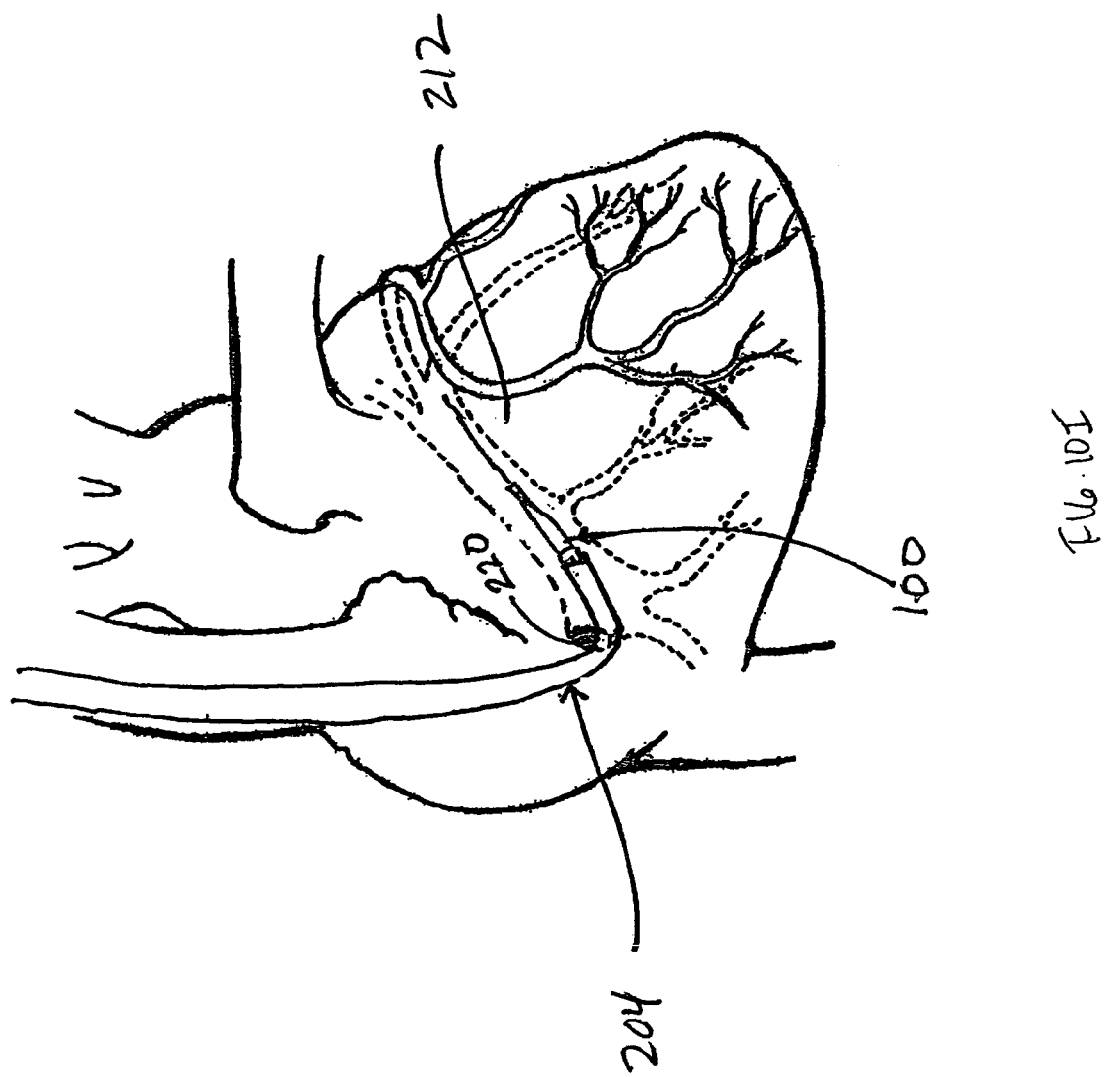

DEFLECTABLE MEDICAL THERAPY DELIVERY DEVICE HAVING COMMON LUMEN PROFILE

CROSS-REFERENCE TO RELATED APPLICATIONS

Cross-reference is hereby made to commonly assigned related U.S. Application, filed concurrently herewith, application Ser. No. 10/656,750, entitled "Deflectable Medical Therapy Delivery Device Having Common Lumen Profle", incorporated herein by reference in it's entirety.

FIELD OF THE INVENTION

The present invention relates generally to a medical therapy delivery device for providing access to a target area of a body, and in particular, the present invention relates to a deflectable catheter having a larger-diameter thru lumen providing direct access by the deflectable catheter to target locations disposed along or at the distal end of tortuous paths of a body.

BACKGROUND OF THE INVENTION

Steerable or deflectable tip cardiovascular catheters are useful in many applications, offering improved maneuverability when compared to catheters with fixed tip curves. A deflectable catheter having a thru lumen has substantial clinical significance in left heart therapy delivery procedures by allowing a guide wire or contrast agent to be used during advancement of a distal tip of the catheter to a target area of a body, such as the coronary sinus and the associated coronary veins. The thru-lumen enables the use of a guide wire and/or contrast agent, which increases the probability of accurate and efficient placement of the catheter and decreases the chance of venous trauma caused by multiple repositioning of the catheter within the tortuous path.

In addition, one or more pull wires, positioned within lumens extending from a handle to the distal end of the catheter, are commonly included within catheters to enable the catheter to be deflected by manipulating the pull wire through the handle, which in turn compresses a distal end of the catheter, creating the deflection along the distal end. When a thru lumen is also incorporated in a catheter having one or more pull wires, the pull wire is segregated from the thru lumen by using separate lumens for the pull wire and the thru lumen. Due to the added wall thickness of the separate lumens, the addition of the pull wire lumen or lumens separate from the thru lumen reduces the amount of area available for the thru lumen, which, unless the outer diameter of the catheter body is increased, reduces the maximum thru lumen diameter, making introduction of a contrast agent or advancement of a guide wire through the thru lumen problematic.

In order to allow passage of the catheter through existing therapy delivery devices, the outer diameter of the deflectable catheter must be 7 French or less. However, such restriction in possible diametric parameters of the catheter make At the same time, the inventors have found that in order to pass enough contrast agent through the thru lumen to be clinically useful, the thru lumen must have a diameter that is greater than 0.021 inches. In addition, the thru lumen must be large enough to allow passage of an introducer type guide wire, which can range in size up to 0.035 inches with 0.025 and 0.035 inches being the most common sized guide wire. All of these dimensional requirements, including the need for a thru lumen for manipulating a pull wire, being sized so as to be able to be advanced through existing therapy delivery devices, being able to pass useful amounts of contrast, and being able to allow passage of an introducer type guide wire, make designing a single catheter with all of these features difficult.

BRIEF DESCRIPTION OF THE DRAWINGS

Other advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

Figure 1:
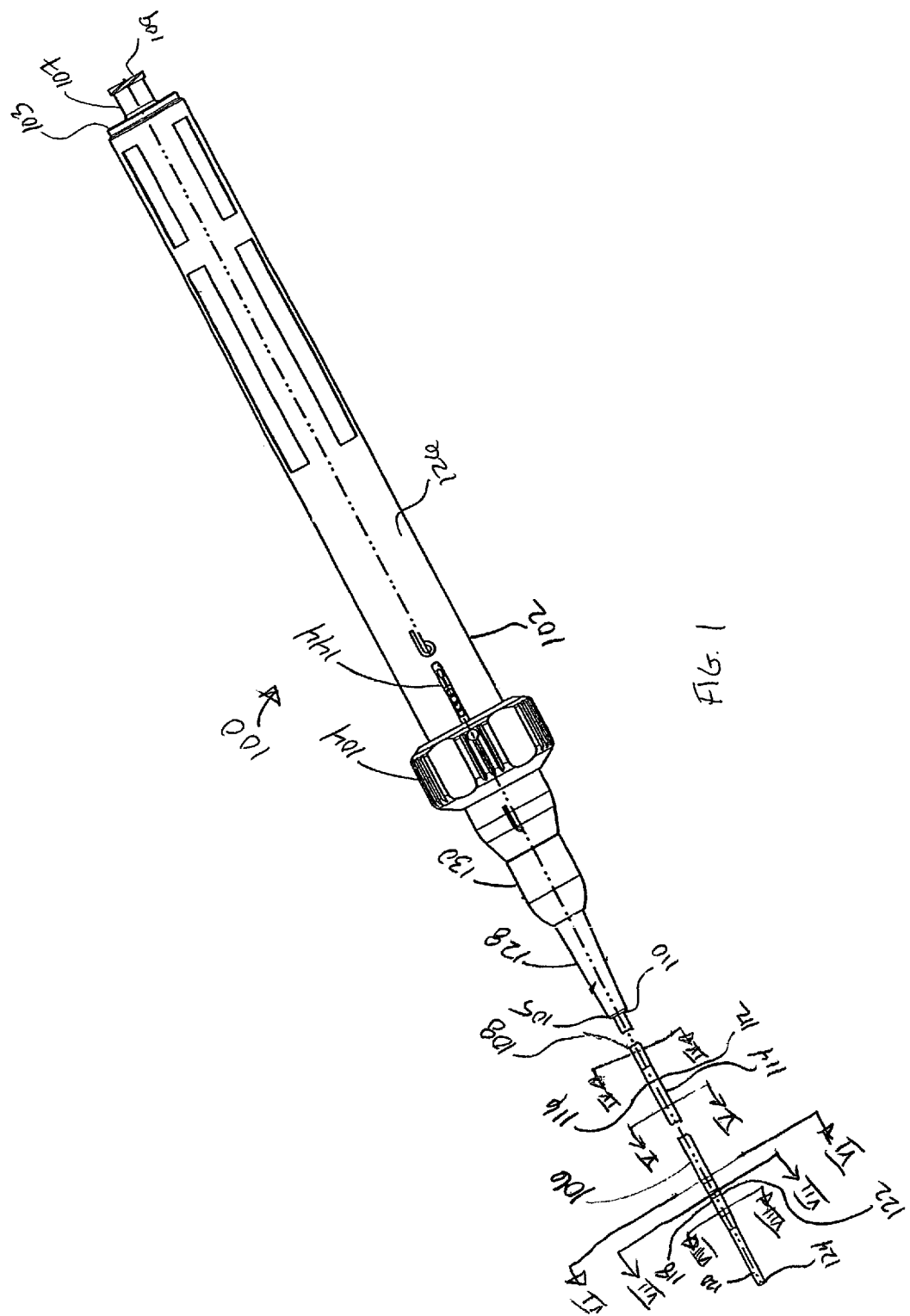
FIG. 1 is a schematic diagram of a medical therapy delivery device according to the present invention.

FIG. 1 is a schematic diagram of a medical therapy delivery device according to the present invention. As illustrated in FIG. 1, a medical therapy delivery device 100 according to the present invention includes a handle 102 and a shaft 106. Handle 102 extends between a proximal end 103 and a distal end 105 and includes a hub 107 located along proximal end 103 that forms an opening 109 for receiving a contrast agent or a guide wire, and a deflection adjustment slide 104. Shaft 106 includes a braided non-deflectable portion 108 extending from a proximal end 110 secured to handle 102 to a distal end 112, a steerable portion 114 extending from a proximal end 116 thermally fused to distal end 112 of non-deflectable portion 108 to a distal end 118, and a soft, non-traumatic deflectable tip 120 extending from a proximal end 122, which is thermally fused to distal end 118 of steerable portion 114, to a distal tip 124. Deflectable tip 120 includes a tapered portion 125 extending along tip 120 between a proximal end 127 and a distal end 129 (see FIG. 3) to facilitate tracking capabilities of device 100 over guide wires, to minimize risk of venous trauma, and to allow for venous sub-selection during advancement of the device 100 within the patient.

Figure 2:
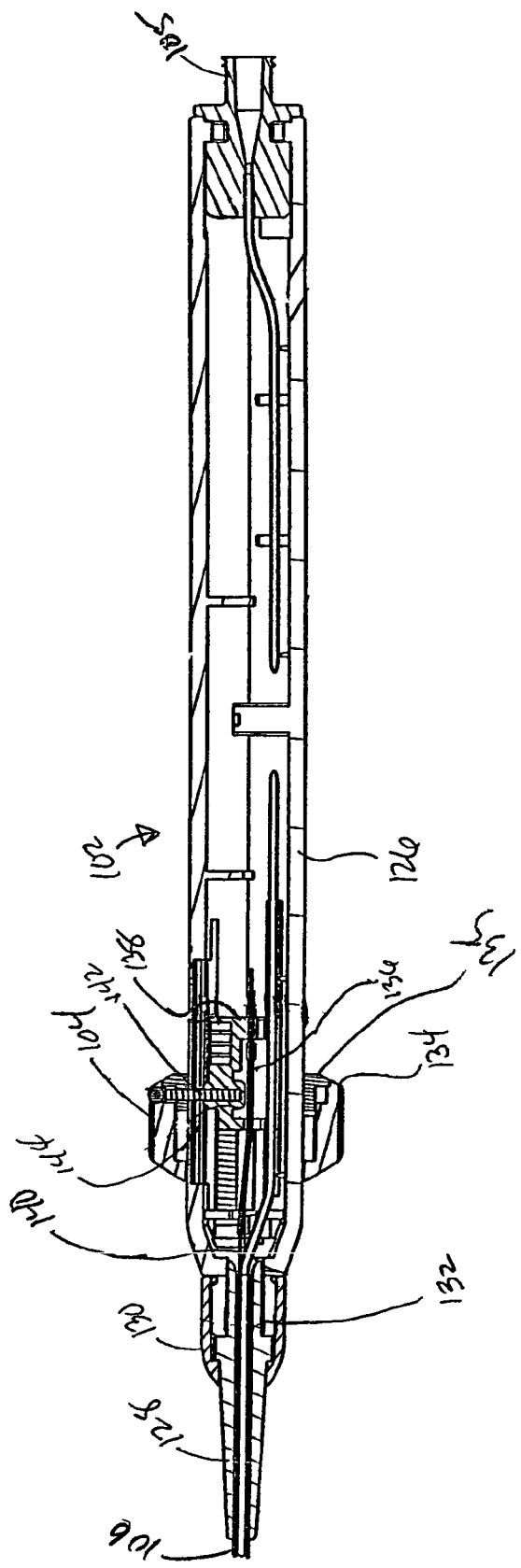
FIG. 2 is a cross-sectional view of a handle of a medical therapy delivery device according to the present invention.

FIG. 2 is a cross-sectional view of a handle of a medical therapy delivery device according to the present invention. As illustrated in FIG. 2 handle 102 further includes a cylindrically shaped housing 126 that is constructed of a rigid material such as ABS, nylon, polycarbonate or polystyrene for example. Shaft 106 is fixed to housing 126 by means of a mechanical grip or an adhesive located along a distal end 132 of housing 126 and incorporating a strain relief 128 and an end cap 130. Slide 104 includes an outer ring 134 and an inner ring 135 being disposed about the periphery of housing with outer ring 134 positioned over inner ring 135 so as to be rotated over inner ring 135 about a central axis of housing 126 and to become fixedly engaged with inner ring 135 when properly rotated relative to inner ring 135 so as to allow both inner ring 134 and outer ring 135 to slide axially along housing 126. A hypotube 136 is secured to a slidable backing plate 138 disposed in the interior of housing 126 and a manipulator wire 140 extends through hypotube 136 to distal end 118 of steerable portion 114 of shaft 106. Manipulator wire 140 and hypotude 136 are joined using an adhesive, or by crimping, for example.

During deflection of steerable portion 114 of shaft 106, which enables shaft 106 to be more easily steered as shaft 106 is advanced within the patient, outer ring 134 is rotated about inner ring 135 and positioned so that an engagement pin 142 is aligned with a slotted opening 144 (shown in FIG. 1), enabling outer ring 134 and inner ring 135 to be slidably advanced axially along housing 126, with the axially advancing of outer ring 134 and inner ring 135 causing corresponding advancement and retraction of backing plate 138, resulting in corresponding advancement and retraction of manipulation wire 140 to thereby adjust deflection of steerable portion 114. One or both of outer ring 134 and inner ring 135 have cam surfaces so that the deflected shape of steerable portion 114 can be retained at a given position by rotating outer ring 134 over inner ring 135, which causes inner ring 135 to be biased against the outer surface of housing 126, thus securing deflection adjustment slide 104 at the desired longitudinal location along handle 102. An example of a handle that may be included in medical therapy delivery device 100 is described in U.S. Pat. No. 6,263,244 to West, incorporated herein by reference in its entirety.

Figure 3:
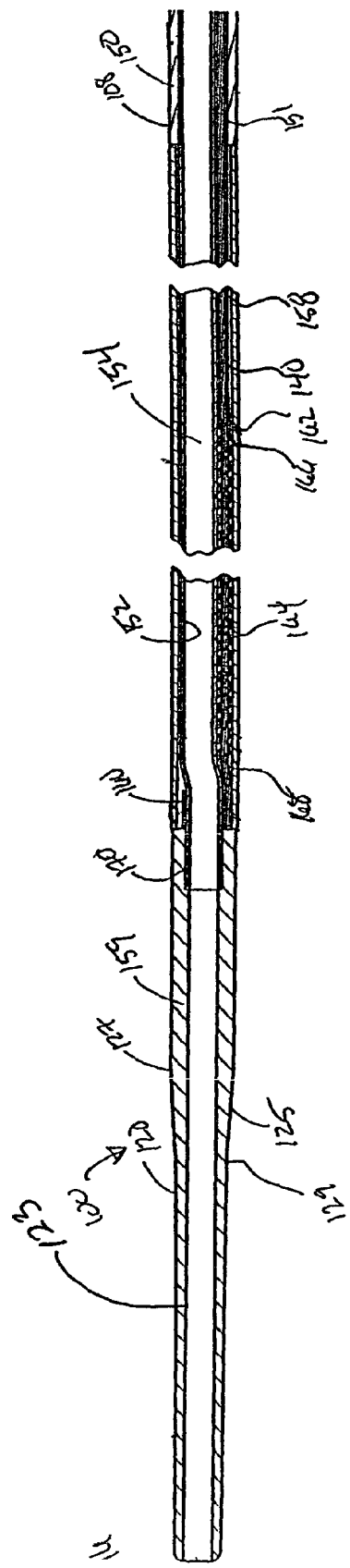
FIG. 3 is a cross-sectional diagram of a shaft of a medical therapy delivery device according to the present invention.

FIG. 3 is a cross-sectional diagram of a shaft of a medical therapy delivery device according to the present invention. As illustrated in FIG. 3, shaft 106 includes an outer insulative layer 150 forming a single shaft lumen 151, described in detail below, a thru lumen tubing 152 forming a thru lumen 154 extending through shaft 106 and handle 102 and in fluid communication with hub 107 (see FIGS. 1 and 2), and a deflection transition tubing 158, positioned within shaft lumen 151 along a portion of steerable portion 114 of shaft 106, forming a wire lumen 166 within which manipulator wire 140 is positioned and through which manipulator wire 140 extends. Insulative layer 150 extends between proximal end 110 of non-deflectable portion 108 and distal end 118 of steerable portion 114 and is formed from a material such as polyether block amide (PEBA), for example. Insulative layer 150 includes a stainless steel braiding and has a Durometer reading of 72D between proximal end 110 and distal end 112 of non-deflectable portion 108, and is non-braided and has a Durometer reading of 40D between proximal end 116 and distal end 118 of steerable portion 114.

Deflectable tip 120 is formed by a deflectable tubing 159 formed of a radio opaque and echo-genic polymer material to allow visualization of deflectable tip 120 using fluoroscopy or ultrasound, while eliminating the need for metallic marker bands or separate radio opaque and echo-genic fillers in the polymer. For example, deflectable tubing 159 is formed by a PEBA material loaded with jet milled tungsten carbide, and has a Durometer reading of 35D between proximal end 122 and distal tip 124. Tubing 159 has a thickness of approximately 0.024 inches extending between proximal end 122 of tubing to proximal end 127 of tapered portion 125, and of approximately 0.012 inches extending between distal end 129 of tapered portion 125 to distal tip, with the thickness of tubing gradually decreasing between proximal end 127 and distal end 129 of tapered portion 125. Tubing 159 forms a tip lumen 123 in fluid communication with thru lumen 154 formed by thru lumen tubing 152 within shaft lumen 151 of shaft 106 and a distal opening 196 formed by tubing 159 at distal tip 124 of deflectable tip 120. Thru lumen tubing 152 is formed by a PEBA material having a Durometer reading of 72D, for example, and deflection transition tubing 158, which extends through steerable portion 114 of shaft 106 from distal end 112 of non-deflectable portion 108 to distal end point 162 along steerable portion 114, is formed of a polyimide material having a Durometer reading of 86D, for example.

In order to fit within the dimensional constraints of existing therapy delivery devices, shaft 106 has an outer diameter of 7 French or less between proximal end 127 of tapered portion 125 and proximal end 110 of non-deflectable portion 108 to allow passage of shaft 106 through currently used guide catheters. Deflectable tip 120 has an outer diameter of 6 French or less between proximal end 127 of tapered portion 125 and distal tip 124 of deflectable tip 120 to facilitate passage of deflectable tip 120 through restricted space, such as the coronary sinus thebesian valve, venous valves, and so forth.

In addition, thru lumen 154 and tip lumen 123 preferably have a common diameter that is large enough to allow passage of introducer type guide wires, with ranges in size of up to 0.035 inches, with 0.025 and 0.035 inches being the most common. At the same time, thru lumen 154 and tip lumen 123 are also formed having a diameter that is large enough to pass clinically useful amounts of contrast, and to enable deflectable tip 120 and shaft 106 to track over a guide wire having a diameter between approximately 0.014 inches and 0.018 inches, preferably 0.016 inches. Applicants have accordingly determined that thru lumen 154 and tip lumen 123 preferably have a diameter of approximately 0.039 inches.

By forming deflectable tip 120 with a lower Durometer material than steerable portion 114, deflectable tip 120 has increased deflectable characteristics, making tip portion 120 passively deflectable (compared to the more active deflectable characteristics of steerable portion 114 through manipulator wire 140), which enables deflectable tip 120 to be more easily tracked over a guide wire or to be deflected so as to be directly advanced to a target site within the patient.

Manipulator wire 140, which has a diameter of approximately 0.009 inches for example, is attached, using welding techniques or soldering for example, to a stainless steel anchoring band 160 positioned along distal end 118 of steerable portion 114 that is fixedly attached to thru-lumen tubing 152.

Deflection transition tubing 158 terminates at end point 162 located along steerable portion 114, and a compressible member 164, such as a spring, is positioned between end point 162 and anchoring band 160 so that manipulator wire 140 extends through compressible member 164 between endpoint 162 and anchoring band 160. Compressible member 164 has an inner diameter of approximately 0.013 inches and an outer diameter of approximately 0.024 inches, for example. In this way, by enclosing manipulator wire 140 within compressible member 164, the larger diameter of compressible member 164 provides a greater area that is engaged against steerable portion 114, thereby increasing the total force for breakthrough of steerable portion 114 when compressed and stressed by manipulator wire 140. In addition, the larger diameter of compressible member 164 helps to maintain the manipulator wire 140 in proper orientation within shaft lumen 151, along steerable portion 114 of shaft 106, during deflection of steerable portion 114 through manipulation of manipulator wire 140.

According to the present invention, compressible member 164, which extends from a proximal end 166 to a distal end 168, may be left unconnected at either of proximal end 166 and proximal end 168, or, in the alternative, steerable portion 114 of outer insulative layer 150 may be adhesively connected to or thermally flowed around distal end 168 of compressible member 164 so that distal end 168 of compressible member 164 is fixedly positioned within shaft 106. In either case, compressible member 164 is free to move relative to manipulator wire 140 and shaft 106 during deflection of steerable portion 114.

In addition, thru lumen tubing 152 is fixed only at a distal end 170 by being thermally fused to proximal end 122 of deflectable tip 120, and is not connected along any other portion of non-deflectable portion 108 and steerable portion 114. As a result, thru lumen tubing 152 is free to slide within shaft 106 during deflection of steerable portion 114 through manipulation of manipulator wire 140 by advancement and retraction of deflection adjustment slide 104 within slotted opening 144 of handle 102.

Figure 4:
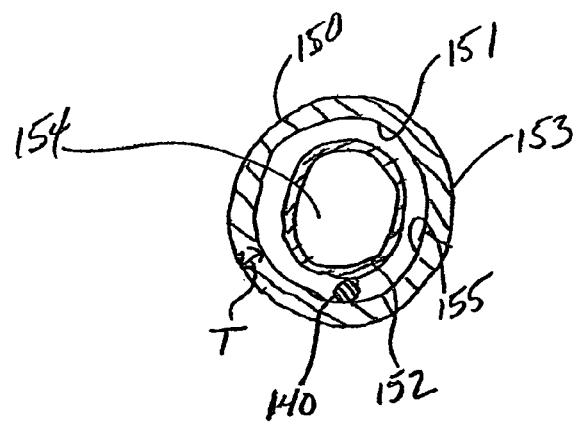
FIG. 4 is a cross-sectional view of a shaft of a medical therapy delivery device according to the present invention, taken along section lines IV-IV of FIG. 1.

FIG. 4 is a cross-sectional view of a shaft of a medical therapy delivery device according to the present invention, taken along section lines IV-IV of FIG. 1. As illustrated in FIGS. 3 and 4, shaft lumen 151 is formed by outer insulative layer 150 to be generally circular in shape between proximal end 110 and distal end 112 of non-deflectable portion 108 of shaft 106. In particular, as illustrated in FIG. 4, outer insulative layer 150 includes an outer wall 153 and an inner wall 155, with inner wall 155 being equally spaced from outer wall 153 so that insulative layer 150 has a generally equal thickness T between proximal end 110 and distal end 112 of non-deflectable portion 108 of shaft 106. For example, according to an embodiment of the present invention, thickness T of insulative layer 150 is approximately 0.014 inches. Shaft lumen 151 has a diameter that enables thru lumen tubing 152 forming thru lumen 154 to be positioned within shaft lumen 151 so that manipulator wire 140 can be positioned to be freely advanced and retracted between an outer wall 157 of thru lumen tubing 152 and inner wall 155 of outer insulative layer 150.

Figure 5:
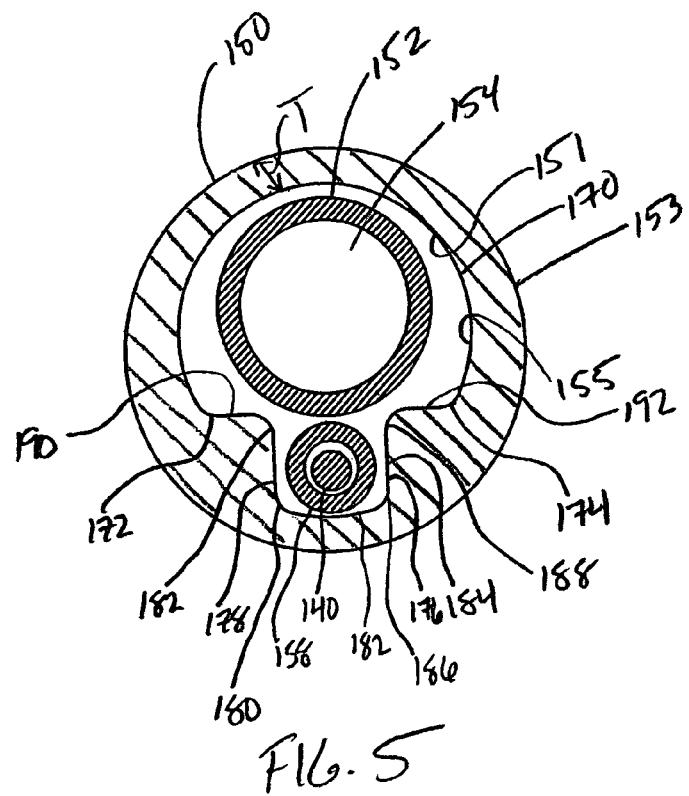
FIG. 5 is a cross-sectional view of a shaft of a medical therapy delivery device according to the present invention, taken along section lines V-V of FIG. 1.

FIG. 5 is a cross-sectional view of a shaft of a medical therapy delivery device according to the present invention, taken along section lines V-V of FIG. 1. As illustrated in FIGS. 3 and 5, manipulator wire 140 is positioned within and extends through deflection transition tubing 158 so that manipulator wire 140 extends outward from endpoint 162 of deflection transition tubing 158 and within shaft lumen 151 along steerable portion 114 to anchoring band 160. Deflection transition tubing 158 is formed of a material having a stiffness that is greater than the stiffness of compressible member 164, such as a polyimide, a stainless steel, a nitinol, or a nylon material, for example, and is generally stiffer than compressible member 164 so that deflection transition tubing 158 provides a stiffness transition between non-deflectable portion 108 and steerable portion 114.

According to a preferred embodiment of the present invention, given the particular stiffness of non-deflectable portion 108 and steerable portion 114 described above, deflection transition tubing 158 has a length of approximately one inch. However, it is understood that the length of deflection transition tubing 158 is dependent upon the stiffness transition deemed necessary, which in turn can depend on various factors, including the difference in stiffness between non-deflectable portion 108 and steerable portion 114. Therefore, the present invention is not intended to be limited to deflection transition tubing 158 having a length of approximately one inch.

According to an embodiment of the present invention, as illustrated in FIGS. 3 and 5, beginning at proximal end 116 of steerable portion 114, inner wall 155 of outer insulative layer 150 of shaft 106 is no longer generally circular in shape throughout and equally spaced from outer wall 153 so that insulative layer 150 has a generally equal thickness T, as is the case between proximal end 110 and distal end 112 of non-deflectable portion 108 of shaft 106. Rather, inner wall 155 includes a first portion 170 that is semi-circular in shape, extending from a first endpoint 172 to a second endpoint 174, and a second portion 176 that is generally rectangular in shape, so that thru lumen tubing 152 forming thru lumen 154 is positioned within first portion 170 and deflection transition tubing 158 and manipulator wire 140 are positioned within second portion 176. Second portion 176 includes a first side wall 178 extending between a first endpoint 180 and a second endpoint 182, substantially parallel to a second side wall 184 extending between a first endpoint 186 and a second endpoint 188, and a curved bottom wall 182 extending between endpoints 180 and 186 of first side wall 178 and second side wall 184, respectively. Finally, a first flange 190 extends between first endpoint 172 of first portion 170 and second endpoint 182 of first side wall 178, and a second flange 192 extends between second endpoint 174 of first portion 170 and second endpoint 188 of second side wall 184 so that thru lumen tubing 152, positioned within first portion 170 of lumen 151, side wall 178 and side wall 184 maintain deflection transition tubing 158 and wire 140 within second portion 176 of lumen 151.

As a result of first flange 190 and second flange 192 being formed by inner wall 155, inner wall 155 of outer insulative layer 150 is spaced from outer wall 153. Consequently, outer insulative layer 150 forms a generally non-equal thickness between proximal end 116 and distal end 118 of steerable portion 114, with an increased thickness, i.e., greater than thickness T around a portion of first portion 170, between outer wall 153 and inner wall 155 around a portion of outer insulative layer 150 that forms second portion 176. The increased thickness resulting from first flange 190 and second flange 192 further aides in the deflection of steerable portion 114 through manipulation of manipulator wire 140 by increasing the total force for breakthrough of steerable portion 114 along a portion of outer insulative layer 150 adjacent to first flange 190 and second flange 192 relative to an area along a portion of outer insulative layer 150 adjacent to bottom wall 182. Thus increased total force for breakthrough along outer insulative layer 150 has the effect of biasing outer insulative layer 150 to deflect in the direction of bottom wall 182 during manipulation of steerable portion 114 through manipulator wire 140.

Figure 6:
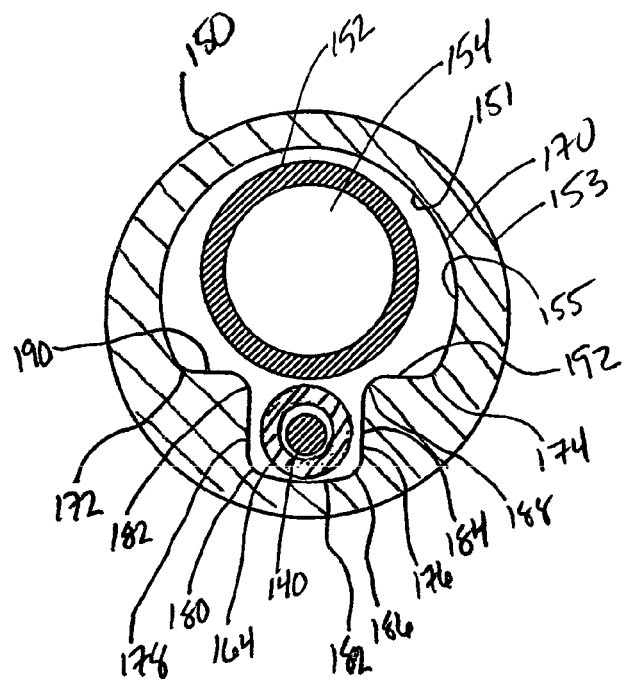
FIG. 6 is a cross-sectional view of a shaft of a medical therapy delivery device according to the present invention, taken along section lines VI-VI of FIG. 1.

FIG. 6 is a cross-sectional view of a shaft of a medical therapy delivery device according to the present invention, taken along section lines VI-VI of FIG. 1. As illustrated in FIGS. 3 and 6, shaft lumen 151 continues to have the same non-circular shape described above, i.e., inner wall 155 includes semi-circular first portion 170 and rectangular second portion 176, as shaft lumen 151 further extends through shaft 106 from endpoint 162 of deflection transition tubing 158 to distal end 118 of steerable portion 114. However, manipulator wire 140 is positioned within compressible member 164 between endpoint 162 and distal end 118, rather than deflection transition tubing 158, so that thru lumen tubing 152, positioned within first portion 170 of lumen 151, side wall 178 and side wall 184 maintain compressible member 164 and manipulator wire 140 within second portion 176 of lumen 151.

Figure 7:
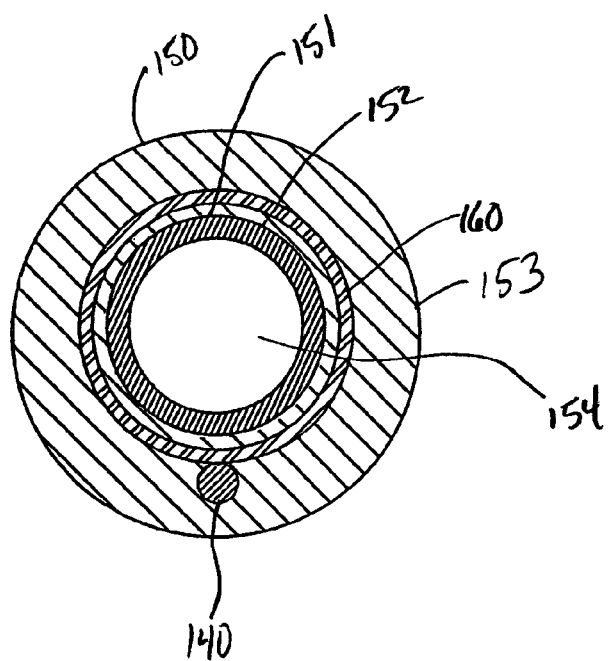
FIG. 7 is a cross-sectional view of a shaft of a medical therapy delivery device according to the present invention, taken along section lines VII-VII of FIG. 1.

FIG. 7 is a cross-sectional view of a shaft of a medical therapy delivery device according to the present invention, taken along section lines VII-VII of FIG. 1. As illustrated in FIGS. 3 and 7, manipulator wire 140 extends outward from distal end 168 of compressible member 164 along distal end 118 of steerable portion 114 and is attached to anchoring band 160 using known means, such as a solder joint or a fuse joint, for example. Both thru lumen tubing 152 and outer insulative layer 150 are thermally flowed around anchoring band 160 to maintain a consistent diameter of shaft 106 and to capture anchoring band 160. As a result of thermally flowing thru lumen tubing 152 and outer insulative layer 150 around anchoring band 160, shaft lumen 151 has a circular shape along shaft 106 at anchoring band 160, with outer insulative layer 150 flowed around thru lumen tubing 152 and manipulator wire 140 so that no gaps are present between thru lumen tubing 152 and outer wall 153.

Figure 8:
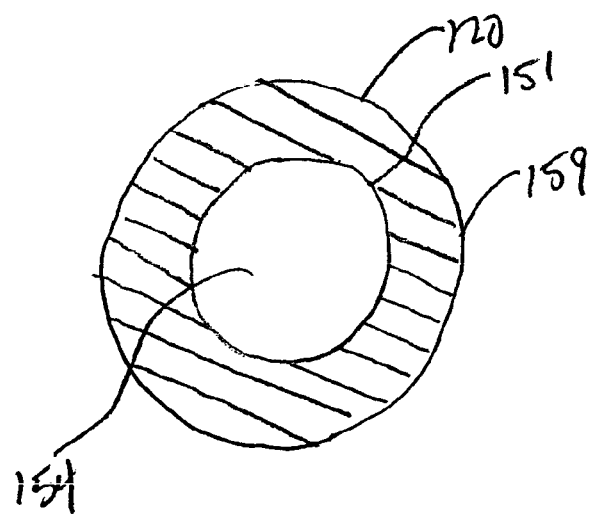
FIG. 8 is a cross-sectional view of a shaft of a medical therapy delivery device according to the present invention, taken along section lines VIII-VIII of FIG. 1.

FIG. 8 is a cross-sectional view of a shaft of a medical therapy delivery device according to the present invention, taken along section lines VIII-VIII of FIG. 1. As illustrated in FIGS. 3 and 8, tip lumen 123 of deflectable tip 120 is formed by deflectable tubing 159 to be generally circular in shape between proximal end 122 and distal tip 124 of deflectable tip 120, and forms distal opening 196 through which a contrast agent injected through thru lumen 154 via opening 109 of hub 107 exits tip lumen 123, or a guide wire passes in or out of tip lumen 123 during insertion of device 100 over the guide wire or extension of guide wire out of device 100 after being inserted through thru lumen 154 via opening 109 of hub 107, respectively.

Figure 9:
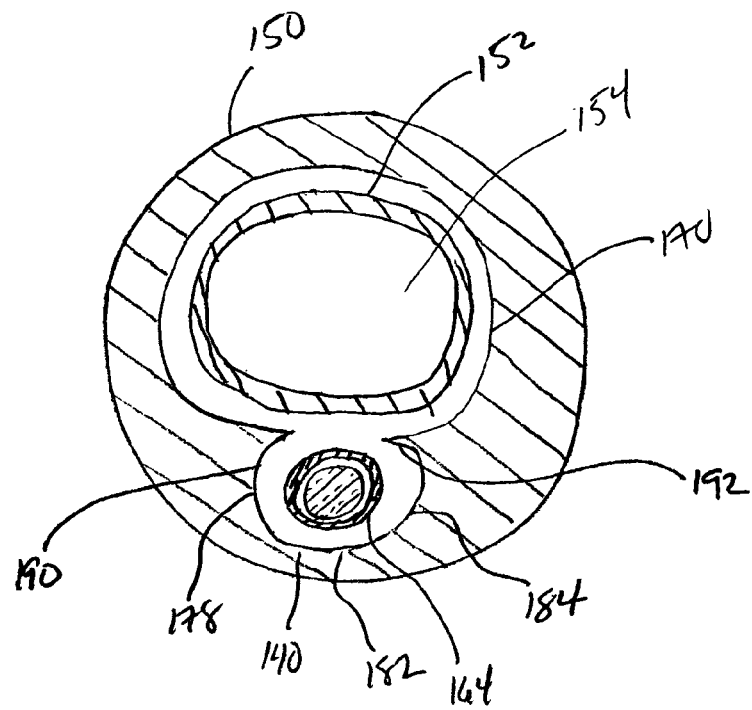
FIG. 9 is a cross-sectional diagram of a shaft of a medical therapy delivery device according to an embodiment of the present invention.

FIG. 9 is a cross-sectional diagram of a shaft of a medical therapy delivery device according to an embodiment of the present invention. It is understood that while second portion 176 of inner wall 155 of outer insulative layer 150 of shaft 106 is described above as being generally rectangular in shape, second portion 176 may have other configurations without departing from the intended scope of the present invention. For example, as illustrated in FIG. 9, according to an embodiment of the present invention, second portion 176 is formed to generally semi-circular in shape, and includes side wall 178, side wall 184, bottom wall 182 and first and second flange 190, 192 so that, depending on the specific location along shaft 106, deflection transition tubing 158, manipulator wire 140 and compressible member 164 are positioned within second portion 176 and maintained within second portion 176 of lumen 151 by lumen tubing 152, positioned within first portion 170 of thru lumen 154, side wall 178 and side wall 184, as described above.

Figure 10C:
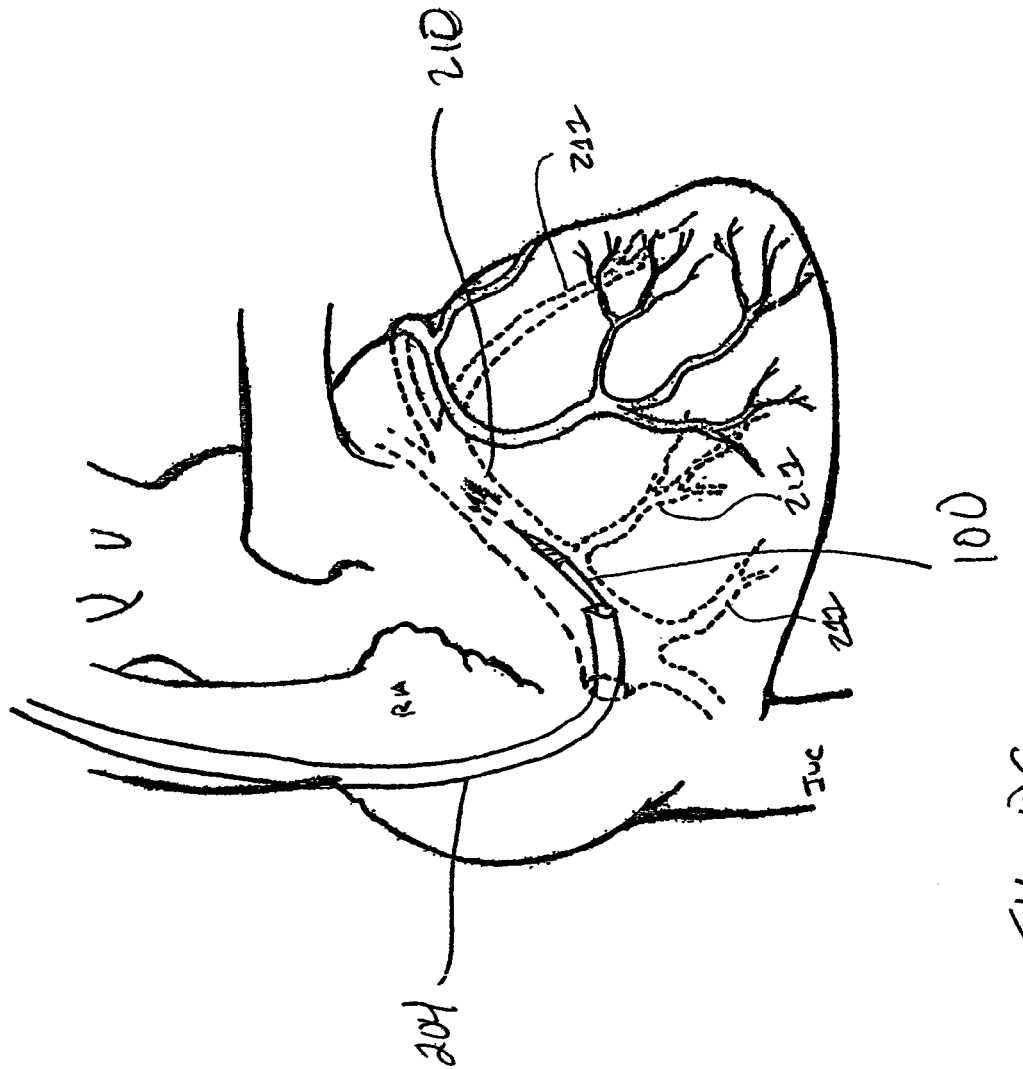
FIGS. 10A-10I are exemplary schematic diagrams illustrating the positioning of a lead within the coronary sinus using a medical therapy delivery device according to the present invention.
Figure 10:
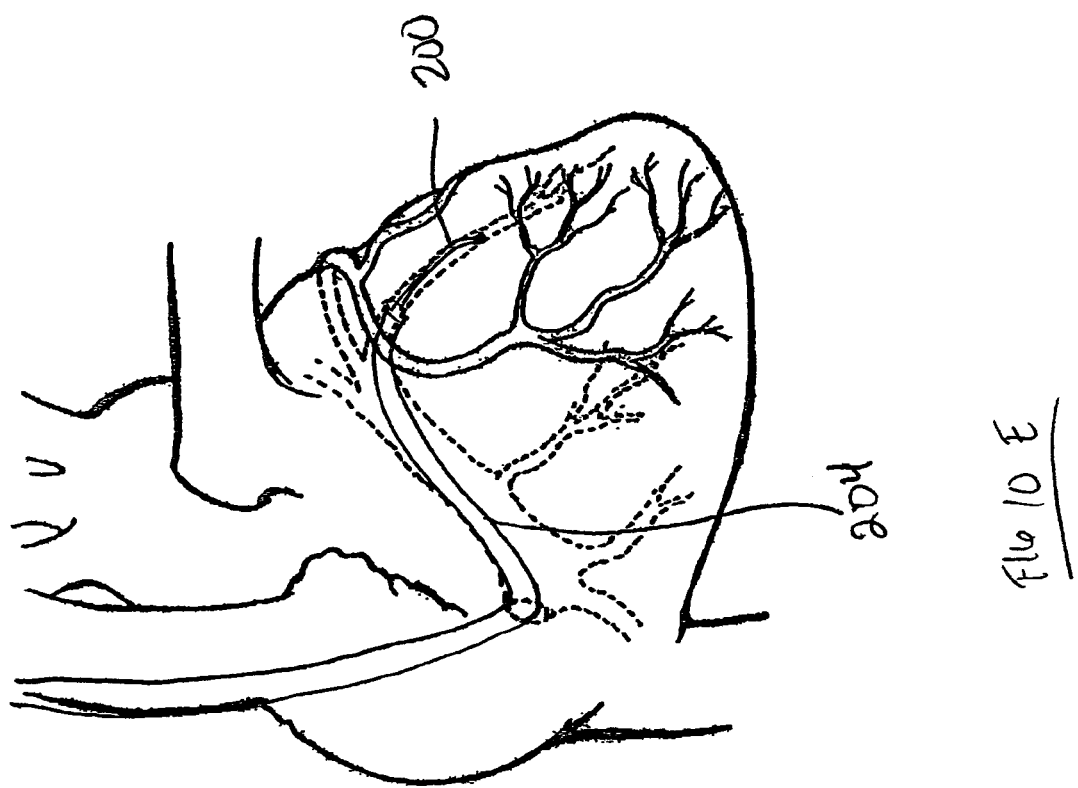

FIGS. 10A-10I are exemplary schematic diagrams illustrating the positioning of a lead within the coronary sinus using a medical therapy delivery device according to the present invention. As illustrated in FIG. 10A, device 100 of the present invention is utilized to locate a target site for delivering a therapy to a patient. For example, device 100 can be used to place an implantable medical device, such as a lead, or to place/deposit other therapies including drugs or biological agents, for example, at a target site. For example, in order to position a lead at a target site within a coronary sinus 202 of a heart 206, a guide catheter 204 is advanced within the atrium of heart 206 through the superior vena cava (SVC).

Once guide catheter 204 is positioned within heart 206, device 100 is inserted within and advanced outward from the distal end of guide catheter 204 and advanced to be positioned within the vicinity of the coronary sinus ostium 208. A contrast agent 210 is then injected through thru lumen 154 of device 100 so that contrast agent 210 advances through thru lumen 154 and is ejected out of distal opening 196 at deflectable tip 120 of device 100, so that the position of coronary sinus ostium 208 can be more accurately identified by the direction of the flow of ejected contrast agent 210, indicated by arrow A. Once contrast agent 210 is injected through device 100 and the flow A of injected contrast agent 210 is observed, device 100 is further advanced upstream through flow A of injected contrast agent 210 and toward coronary sinus ostium 208 so that deflectable tip 120 of device 100 is advanced directly through coronary sinus ostium 208 and is positioned within coronary sinus 202.

According to an embodiment of the present invention, in situations where the position of coronary sinus ostium 208 can be identified using techniques other than the injection of contrast agent 210, tapered portion 125 of deflectable tip 120, and the non-traumatic characteristic and decreasing thickness of tubing 159 forming deflectable tip 120 enable deflectable tip 120 to be advanced directly to the coronary sinus ostium 208 without injecting contrast agent 210. Device 100 is either advanced directly within heart 206 and to coronary sinus ostium 208, or is advanced within heart 206 and to coronary sinus ostium 208 through guide catheter 204. Deflectable tip 120 is then advanced through coronary sinus ostium 208 and within coronary sinus 202 either directly or over a guide wire 212 (FIG. 10B) that is advanced outward from deflectable tip 120 of device 100, through coronary sinus ostium 208 and positioned within coronary sinus 202 as described below.

As illustrated in FIG. 10B, according to an embodiment of the present invention, once contrast agent 210 is injected through device 100 and the flow A of injected contrast agent 210 is observed, a guide wire 212 is inserted within and advanced through thru lumen 154 of device 100 and outward from distal opening 196 at deflectable tip 120 of device 100. Guide wire 212 is further advanced upstream through flow A of injected contrast agent 210 and toward coronary sinus ostium 208 so that guide wire 212 is advanced through coronary sinus ostium 208 and is positioned within coronary sinus 202. Deflectable tip 120 of device 100 is then tracked over guide wire 212 so that device 100 is positioned within coronary sinus 202.

On the other hand, guide wire 212 may be already positioned within thru lumen 154 when device 100 is initially advanced within the patient. Because of the increased size of thru lumen 154 of the present invention, contrast agent 210 can then be injected through thru lumen 154 of device 100 so that contrast agent 210 advances through and is ejected out of distal opening 196 at deflectable tip 120 while guide wire 212 is positioned within thru lumen 154. Guide wire 212 is then further advanced so as to be extended outward from distal opening 196 of deflectable tip 120 and through flow A of injected contrast agent 210 and toward coronary sinus ostium 208, enabling guide wire 212 to be advanced through coronary sinus ostium 208 and positioned within coronary sinus 202. Once guide wire is positioned within coronary sinus 202, device 100 is then advanced within coronary sinus 202 over guide wire 212. As a result of tapered portion 125 being included along deflectable tip 120, and the non-traumatic characteristic and decreasing thickness of tubing 159 forming deflectable tip 120, deflectable tip 120 is more easily further advanced over guide wire 212, so that device 100 can be more easily tracked over guide wire 212 and into coronary sinus 202.

As illustrated in FIG. 10C, once device 100 is positioned within coronary sinus 202 with or without the use of contrast agent 210 and either directly or with the use of guide wire 212, guide catheter 204 is advance over device 100 and positioned within coronary sinus 202. As a result of tapered portion 125 being included along deflectable tip 120, and the non-traumatic characteristic and decreasing thickness of tubing 159 forming deflectable tip 120, deflectable tip 120 enables device 100 to be more easily further advanced outward from the distal end of guide catheter 204 and within coronary sinus 202 so that once device 100 is fully advanced within coronary sinus 202, contrast agent 210 can be injected out of distal opening 196 at deflectable tip 120 of device 100 so that the contour of coronary sinus 202 and one or more of coronary sinus veins 211 can be more accurately identified by the direction of the flow of contrast agent 210. In particular, for example, once deflectable tip 120 is advanced within coronary sinus 120, contrast agent 210 is injected out of distal opening 196 and an image is taken showing flow of contrast agent 210. Deflectable tip 120 is then either further advanced or retracted and contrast agent 210 is again injected out of distal opening 196 and an image is taken showing flow of contrast agent 210. In this way, a target site within coronary sinus 202 or within one of veins 211 can be located using one or a series of local venograms.

As illustrated in FIG. 10D, once the target site is located using contrast agent 210 injected through thru lumen 154 of device 100, device 100 is advanced to the target site. Guide catheter 204 is then advanced over device 100 to the ostium of one of veins 211 associated with the target site, device 100 is subsequently removed from guide catheter 204, and lead 200 is advanced to the target site through guide catheter 204 so that an electrode 214 is placed at the target site. Guide catheter 204 is then removed, leaving lead 200 positioned in place at the target site.

By enabling contrast agent 210 to be injected through thru lumen 154 of device 100, the present invention eliminates the need for removing device from guide catheter 204 once guide catheter is positioned within coronary sinus 202 and inserting a separate venogram balloon catheter within coronary sinus 202 via guide catheter 204 to inject contrast agent 210.

According to another embodiment of the present invention, as illustrated in FIG. 10E, as a result of tapered portion 125 being included along deflectable tip 120, and the non-traumatic characteristic and decreasing thickness of tubing 159 forming deflectable tip 120, once the target site is located using contrast agent 210 injected through thru lumen 154 of device 100, deflectable tip 120 can be directly advanced through coronary sinus 208 and within vein 212 corresponding to the target site, so that once device 100 is positioned within vein 212, guide catheter 204 can then be advanced to the target site over device 100. Device 100 is then removed from guide catheter 204 and lead 200 is advanced to the target site through guide catheter 204 so that an electrode 214 is placed at the target site. Guide catheter 204 is then removed, leaving lead 200 positioned in place at the target site.

Furthermore, according to another embodiment of the present invention, guide wire 212 could either be positioned within thru lumen 154 during ejection of contrast agent 210 within coronary sinus 202, or inserted through thru lumen 154 after injection of contrast agent 210 through thru lumen 154, and subsequently advanced to the target site. As a result of tapered portion 125 being included along deflectable tip 120, and the non-traumatic characteristic and decreasing thickness of tubing 159 forming deflectable tip 120, deflectable tip 120 is more easily further advanced over guide wire 212 within coronary sinus 202, so that device 100 can be more easily tracked over guide wire 212 to the target site. Guide catheter 204 is advanced to the target site over device 100, and device 100 is then removed from guide catheter 204 and lead 200 is advanced to the target site through guide catheter 204 so that an electrode 214 is placed at the target site. Guide catheter 204 is then removed, leaving lead 200 positioned in place at the target site.

Figure 10F:
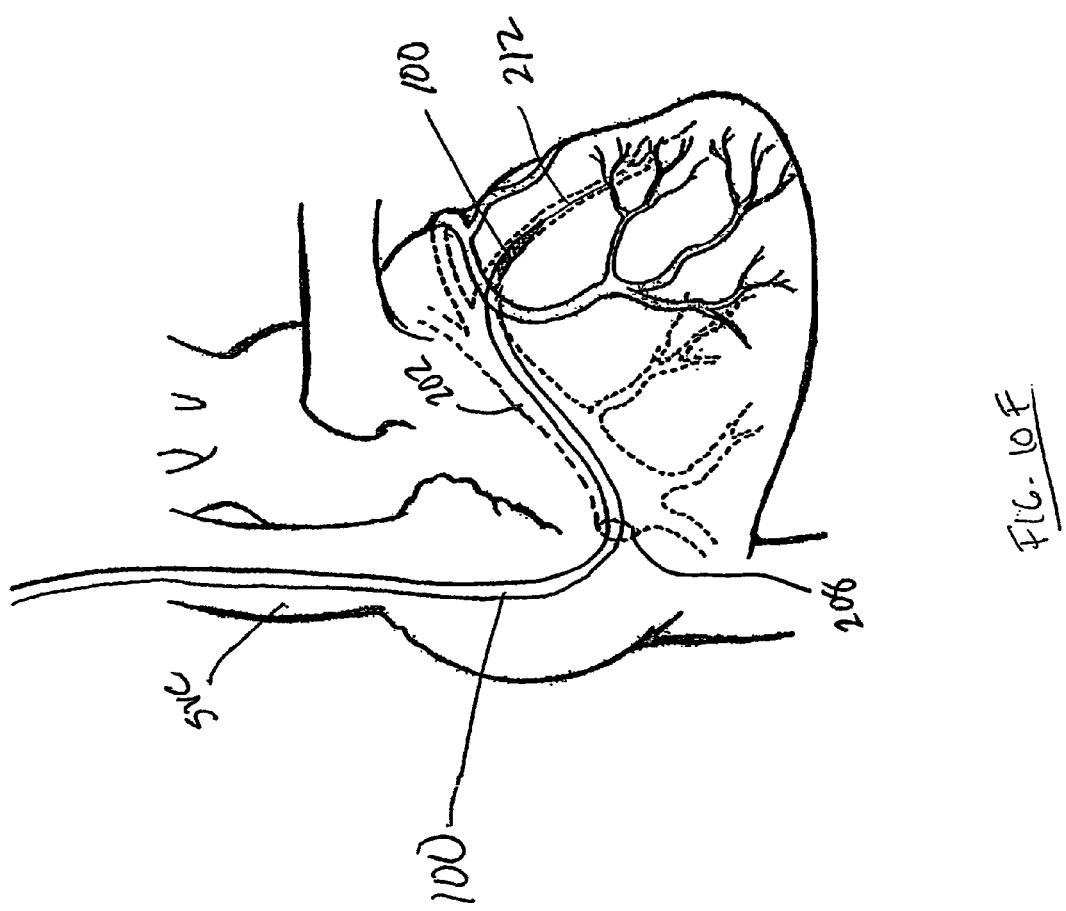

As illustrated in FIG. 10F, as a result of tapered portion 125 being included along deflectable tip 120, and the non-traumatic characteristic and decreasing thickness of tubing 159 forming deflectable tip 120, device 100 can be inserted directly within coronary sinus 202 and the lead can be positioned at the target site without utilizing guide catheter 204. In particular, device 100 is advanced within the atrium of heart 206 through SVC and positioned within the area of coronary sinus 202. Contrast agent 210 is then injected through thru lumen 154 of device 100 to locate coronary sinus ostium 208. Once coronary sinus ostium 208 is located, deflectable tip 120 of device 100 is advanced through coronary sinus ostium 208 and within coronary sinus 202 directly, or guide wire 212 is advanced within coronary sinus 202 through coronary sinus ostium 208 and deflectable tip 120 of device 100 is advanced over guide wire 212 to position device 100 within coronary sinus 202. Once device 100 is positioned within coronary sinus 202, contrast agent 210 is injected through thru lumen 154 in order to located the target site within one of veins 211 of coronary sinus 202, as described above. Deflectable tip 120 is then further advanced within coronary sinus 202 towards the target site and guide wire 212 is then extended from distal tip 196 of deflectable tip 120 to the target site, or guide wire 212 is extended from distal tip 196 of deflectable tip 120 to the target site directly, without further advancement of deflectable tip 120 within coronary sinus 202. Once guide wire 212 is positioned at the target site, device 100 is removed, leaving guide wire 212 in place, and lead 200 is advanced to the target site over guide wire 212. Once lead 200 is positioned at the target site, guide wire 212 is removed.

As a result, by eliminating the need for utilizing guide catheter 204, the present invention eliminates having to slit guide catheter 204 so that guide catheter 204 can be removed from lead 200 and over connectors (not shown) of lead 200, as required in current known lead placement systems.

Since tapered portion 125 is included along deflectable tip 120, and the non-traumatic characteristic and decreasing thickness of tubing 159 forming deflectable tip 120, making deflectable tip 120 more easily advanceable over guide wire 212, device 100 of the present invention reduces the difficulty of cannulating coronary sinus 202 in patients where coronary sinus ostium 208 is partially occluded by the thebesian valve 220, for example, or is occluded more distally in vasculature of coronary sinus 202. In such cases, when advancing device 100 to coronary sinus ostium 208, as described above, contrast agent 210 injected through thru lumen 154 of device 100 enables a pathway around the occlusion 220 to be more easily identified. In the same way, contrast agent 210 injected through thru lumen 154 of device 100 when device 100 is positioned within coronary sinus 202 enables a pathway around a more distally located occlusion.

Once the pathway is identified, guide wire 212 is advanced around occlusion 220 through the pathway and into coronary sinus 202. As illustrated in FIGS. 10G and 10H, once guide wire 212 is advanced past occlusion 220 and positioned distally from occlusion 220 within coronary sinus 202, deflectable tip 120 of device 100 is then advanced past occlusion 220 over guide 212 so that device 100 is advanced distally within coronary sinus 202 to locate the target site, using the methods described above.

As illustrated in FIG. 101, once device 100 is advanced distally from occlusion 220 and within coronary sinus 202, guide catheter 204 is then advanced over device 100, past occlusion 220 and distally within coronary sinus 202. In this way, device 100 acts as a bridge between thin maneuverable guide wire 212 and thicker, stiffer guide catheter 204 to reduce the difficulty in advancing guide catheter 204 past occlusion 220. Contrast agent 210 (not shown in FIG. 101) may then be injected through thru lumen 154 of device 100 to identify the target site and position lead 200 at the target site using any of the methods described above.

In addition, lead 200 could be positioned beyond occlusion 220 without utilizing guide catheter 200, as described above in reference to FIG. 10F, so that device 100 is inserted directly within coronary sinus 202 by injecting contrast agent 210 through thru lumen 154 of device 100 to locate coronary sinus ostium 208 and occlusion 220. Once a pathway around occlusion 220 is identified, guide wire 212 is advanced through the pathway and distally within coronary sinus 202 beyond occlusion 220, and deflectable tip 120 of device 100 is then advanced past occlusion 220 over guide 212 and device 100 is advanced distally within coronary sinus 202 to locate the target site, using the methods described above. In any case, guide wire 212 is then placed at the target site, either directly by being advanced distally outward from delivery device 100, or through delivery device 100 once delivery device 100 is located at the target site, as described above, device 100 is then removed, leaving guide wire 212 in place. Lead 200 is then advanced to the target site over guide 212. Once lead 200 is positioned at the target site, guide wire 212 is removed.

It is understood that although device 100 is described above as being advanced within coronary sinus ostium 208 by first injecting contrast agent 210 through thru lumen 154, as a result of steerable portion 114 of device 100, tapered portion 125 being included along deflectable tip 120, and the non-traumatic characteristic and decreasing thickness of tubing 159 forming deflectable tip 120, deflectable tip 120 can be used to directly locate and cannulate coronary sinus ostium 208 without injecting contrast agent 210 to locate ostium 208 by the resulting view of the flow of contrast agent 210.

While a particular embodiment of the present invention has been shown and described, modifications may be made. It is therefore intended in the appended claims to cover all such changes and modifications, which fall within the true spirit and scope of the invention.

The invention claimed is:

1. A method of locating a target site within a coronary sinus or a coronary sinus branch vein for delivering a therapy to a patient, comprising:
    advancing a delivery device having a steerable portion and a deflectable tip having a tapered portion to an area downstream from the coronary sinus, the coronary sinus downstream from the target site;
    further advancing the delivery device within the area and toward the coronary sinus;
    delivering a contrast medium from a distal end of the delivery device within the area to locate the coronary sinus by observing the direction of the flow of the delivered contrast medium in the area away from the coronary sinus; and
    further advancing the delivery device upstream through the direction of the flow of the contrast medium into the coronary sinus.

2. The method of claim 1, further comprising delivering a contrast medium through a thru lumen and outward from a distal end of the delivery device in fluid communication with the thru lumen to position the contrast medium along the coronary sinus or the coronary sinus branch vein.

3. The method of claim 1, further comprising:
    advancing the delivery device to the target site;
    advancing a guide wire through the thru lumen of the delivery device to the target site; and
    advancing a pacing lead to the target site over the guide wire.

4. The method of claim 1, further comprising:
    advancing a guide wire to the target site through the thru lumen of the delivery device and the contrast medium delivered within the coronary sinus; and
    advancing a pacing lead to the target site over the guide wire.

5. The method of claim 1, wherein advancing the delivery device to the area downstream from the coronary sinus comprises:
    advancing a guide catheter within the patient; and
    advancing the delivery device to the area along the coronary sinus via the guide catheter.

6. The method of claim 3, further comprising inserting the guide wire within the thru lumen prior to advancing the delivery device to the area downstream from the coronary sinus.

7. The method of claim 1, further comprising advancing a guide catheter within the patient, wherein advancing the delivery device to the area downstream from the coronary sinus includes advancing the delivery device through and outward from a distal end of the guide catheter.

8. The method of claim 7, further comprising advancing the guide catheter within the coronary sinus over the delivery device.

9. The method of claim 8, further comprising:
    advancing the delivery device to the target site utilizing the contrast medium delivered within the coronary sinus;
    advancing the guide catheter over the delivery device to the target site;
    removing the delivery device from the guide catheter; and
    delivering the therapy to the target site through the guide catheter.

10. The method of claim 1, further comprising manipulating a manipulator wire during the advancing of the delivery device, wherein the delivery device includes a single shaft lumen having a first lumen portion positioned about the thru lumen and a second lumen portion, offset from and in fluid communication with the first lumen portion, the second lumen portion having a first side wall, a second side wall and a bottom wall extending between the first side wall and the second side wall, the thru lumen, the first side wall, the second side wall and the bottom wall positioning the manipulator wire within the second lumen portion.

11. The method of claim 1, wherein advancing the delivery device within the coronary sinus or a coronary sinus branch vein comprises:
    advancing a guide wire outward from the distal end through the thru lumen of the delivery device and within the coronary sinus or the coronary sinus branch vein; and
    advancing the delivery device over the guide wire.

12. A method of locating a target site along the cardiovascular system for delivering a therapy to a patient, comprising:
    advancing a delivery device having a steerable portion and a deflectable tip having a tapered portion to an area downstream from a coronary sinus, the coronary sinus downstream from -the target site;

delivering a contrast medium through a thru lumen and outward from a distal end of the delivery device in fluid communication with the thru lumen to position the contrast medium along the coronary sinus;
further advancing the delivery device within the area and toward the coronary sinus;
delivering the contrast medium from the distal end of the delivery device within the area to locate the coronary sinus by observing the direction of the flow of the delivered contrast medium in the coronary sinus away from the coronary sinus; and
further advancing the delivery device from the area upstream through the direction of the flow into the coronary sinus.

13. The method of claim 12, further comprising delivering a contrast medium through a thru lumen and outward from a distal end of the delivery device in fluid communication with the thru lumen to position the contrast medium along the coronary sinus.

14. The method of claim 12, further comprising:
advancing the delivery device to the target site;
advancing a guide wire through the thru lumen of the delivery device to the target site; and
advancing a pacing lead to the target site over the guide wire.

15. The method of claim 12, further comprising:
advancing a guide wire to the target site through the thru lumen of the delivery device; and
advancing a pacing lead to the target site over the guide wire.

16. The method of claim 12, wherein advancing the delivery device to the area along the coronary sinus comprises:
advancing a guide catheter within the patient; and
advancing the delivery device to the area downstream from the coronary sinus via the guide catheter.

17. The method of claim 14, further comprising inserting the guide wire within the thru lumen prior to advancing the delivery device to the area downstream from the coronary sinus.

18. The method of claim 12, further comprising advancing a guide catheter within the patient, wherein advancing the delivery device to the area downstream from the coronary sinus includes advancing the delivery device through and outward from a distal end of the guide catheter.

19. The method of claim 18, further comprising advancing the guide catheter within the coronary sinus over the delivery device.

20. The method of claim 19, further comprising:
advancing the delivery device to the target;
advancing the guide catheter over the delivery device to the target site;
removing the delivery device from the guide catheter; and
delivering the therapy to the target site through the guide catheter.

21. The method of claim 12, further comprising manipulating a manipulator wire during the advancing of the delivery device, wherein the delivery device includes a single shaft lumen having a first lumen portion positioned about the thru lumen and a second lumen portion, offset from and in fluid communication with the first lumen portion, the second lumen portion having a first side wall, a second side wall and a bottom wall extending between the first side wall and the second side wall, the thru lumen, the first side wall, the second side wall and the bottom wall positioning the manipulator wire within the second lumen portion.

22. The method of claim 12, wherein advancing the delivery device within the coronary sinus comprises:
advancing a guide wire outward from the distal end through the thru lumen of the delivery device and within the coronary sinus; and
advancing the delivery device over the guide wire.

23. A method of locating a target site along the cardiovascular system for delivering a therapy to a patient, comprising:
advancing a delivery device having a steerable portion and a deflectable tip having a tapered portion to an area downstream from a coronary sinus, the coronary sinus downstream from the target site;
adjusting deflection of a first portion of the delivery device relative to a second portion of the delivery device via a manipulator wire;
delivering a contrast medium through a thru lumen and outward from a distal end of the delivery device in fluid communication with the thru lumen to position the contrast medium along the coronary sinus;
further advancing the delivery device within the area and toward the coronary sinus;
delivering the contrast medium from the distal end of the delivery device within the area to locate the coronary sinus by observing the direction of the flow of the delivered contrast medium in the area away from the coronary sinus; and
further advancing the delivery device from the area upstream through the direction of the flow into the coronary sinus,
wherein the delivery device includes a single shaft lumen having a first lumen portion positioned about the thru lumen and a second lumen portion, offset from and in fluid communication with the first lumen portion, the second lumen portion having a first side wall, a second side wall and a bottom wall extending between the first side wall and the second side wall, the thru lumen, the first side wall, the second side wall and the bottom wall positioning the manipulator wire within the second lumen portion, and wherein the delivery device has an outer diameter of 7 French or less between a proximal end of the delivery device and a proximal end of the tapered portion, and the deflectable tip has an outer diameter of 6 French or less between the proximal end of the tapered portion and the distal tip.

24. The method of claim 23, further comprising:
advancing the delivery device to the target site;
advancing a guide wire through the thru lumen of the delivery device to the target site; and
advancing a pacing lead to the target site over the guide wire.

25. The method of claim 23, further comprising:
advancing a guide wire to the target site through the thru lumen of the delivery device; and
advancing a pacing lead to the target site over the guide wire.

26. The method of claim 23, wherein advancing the delivery device to the area along the coronary sinus comprises:
advancing a guide catheter within the patient; and
advancing the delivery device to the area downstream from the coronary sinus via the guide catheter.

27. The method of claim 24, further comprising inserting the guide wire within the thru lumen prior to advancing the delivery device to the area downstream from the coronary sinus.

28. The method of claim 23, further comprising advancing a guide catheter within the patient, wherein advancing the delivery device to the area downstream from the coronary sinus includes advancing the delivery device through and outward from a distal end of the guide catheter.

29. The method of claim 28, further comprising advancing the guide catheter within the coronary sinus over the delivery device.

30. The method of claim 29, further comprising:
advancing the delivery device to the target;
advancing the guide catheter over the delivery device to the target site;
removing the delivery device from the guide catheter; and
delivering the therapy to the target site through the guide catheter.

31. The method of claim 23, wherein advancing the delivery device within the coronary sinus comprises:
advancing a guide wire outward from the distal end through the thru lumen of the delivery device and within the coronary sinus; and
advancing the delivery device over the guide wire.

32. A method of locating a target site within the coronary sinus or a coronary sinus branch vein for delivering a therapy to a patient, comprising:
advancing a delivery device having a steerable portion and a deflectable tip having a tapered portion within an atrium of a heart of the patient;
further advancing the delivery device toward the coronary sinus ostium;
delivering a contrast medium from a distal end of the delivery device within the heart to locate the coronary sinus ostium, the coronary sinus ostium location being identified by observing the direction of flow of the contrast medium within the atrium away from the coronary sinus ostium; and
advancing the delivery device upstream through the flow of the contrast medium and into the coronary sinus.

33. A method of locating a target site within the coronary sinus or a coronary sinus branch vein for delivering a therapy to a patient through a delivery device configured to eliminate a need for removing the delivery device from a guide catheter once the guide catheter is positioned within the coronary sinus, the method comprising:
advancing a delivery device having a steerable portion and a deflectable tip having a tapered portion within an atrium of a heart of the patient;
further advancing the delivery device toward the coronary sinus ostium;
delivering a contrast medium from a distal end of the delivery device within the heart to locate the coronary sinus ostium, the coronary sinus ostium location being identified by observing the direction of flow of the contrast medium within the atrium away from the coronary sinus ostium; and
advancing the delivery device upstream through the flow of the contrast medium and into the coronary sinus.

34. A method of locating a target site within the coronary sinus or a coronary sinus branch vein for delivering a therapy to a patient through a delivery device configured to eliminate a need for delivery of a separate venogram balloon catheter within the coronary sinus via the guide catheter to inject contrast agent, the method comprising:
advancing a delivery device having a steerable portion and a deflectable tip having a tapered portion within an atrium of a heart of the patient;
further advancing the delivery device toward the coronary sinus ostium;
delivering a contrast medium from a distal end of the delivery device within the heart to locate the coronary sinus ostium, the coronary sinus ostium location being identified by observing the direction of flow of the contrast medium within the atrium away from the coronary sinus ostium; and
advancing the delivery device upstream through the flow of the contrast medium and into the coronary sinus.

35. The method of claim 12, wherein advancing the delivery device to the area along the coronary sinus comprises:
moving a guide catheter within the patient; and
moving the delivery device to the area downstream from the coronary sinus via the guide catheter.

36. A method of locating a target site within a coronary sinus or a coronary sinus branch vein for delivering a therapy to a patient in which the delivery device is configured to eliminate a need for delivery of a separate venogram balloon catheter within the coronary sinus via the guide catheter to inject contrast agent, the method comprising, comprising:
moving a delivery device having a steerable portion and a deflectable tip having a tapered portion to an area near the coronary sinus;
delivering a contrast medium from a distal end of the delivery device within the area to locate the coronary sinus by observing the direction of the flow of the delivered contrast medium in the area away from the coronary sinus; and
further moving the delivery device through the direction of the flow of the contrast medium into the coronary sinus.

* * * * *